(12) United States Patent
Kynor et al.

(10) Patent No.: US 7,561,051 B1
(45) Date of Patent: Jul. 14, 2009

(54) MAGNET LOCATING APPARATUS AND METHOD OF LOCATING A MAGNET USING SUCH APPARATUS

(75) Inventors: David B. Kynor, Sharon, VT (US); Marc A. Kenton, Hanover, NH (US)

(73) Assignee: Creare Inc., Hanover, NH (US)

( * ) Notice: Subject to any disclaimer, the term of this patent is extended or adjusted under 35 U.S.C. 154(b) by 231 days.

(21) Appl. No.: 11/406,113

(22) Filed: Apr. 18, 2006

Related U.S. Application Data

(60) Provisional application No. 60/673,558, filed on Apr. 20, 2005.

(51) Int. Cl.
*G08B 13/14* (2006.01)

(52) U.S. Cl. .................. 340/572.6; 340/572.4; 600/424

(58) Field of Classification Search .............. 340/572.1, 340/572.2, 572.4, 572.5, 572.8, 686.1, 691.1, 340/573.1; 600/117, 424, 407, 420; 128/898, 128/899, 653.1

See application file for complete search history.

(56) References Cited

U.S. PATENT DOCUMENTS

| | | | |
|---|---|---|---|
| 2,393,717 A | 1/1946 | Speaker ...................... | 128/1.5 |
| 3,460,528 A | 8/1969 | Carney ....................... | 128/2.1 |
| 3,847,157 A | 11/1974 | Caillouette et al. .......... | 128/348 |
| 4,317,078 A | 2/1982 | Weed et al. .................. | 324/208 |
| 4,416,289 A | 11/1983 | Bresler ........................ | 128/737 |
| 4,431,005 A | 2/1984 | McCormick ................ | 128/656 |
| 4,445,501 A | 5/1984 | Bresler ........................ | 128/1.5 |
| 4,905,698 A | 3/1990 | Strohl, Jr. et al. ........... | 128/653 |
| 4,943,770 A | 7/1990 | Ashley-Rollman | |
| | | et al. ...................... | 324/207.17 |
| 5,099,845 A | 3/1992 | Besz et al. ................ | 128/653.1 |
| 5,125,888 A | 6/1992 | Howard et al. ................ | 600/12 |
| 5,253,647 A | 10/1993 | Takahashi et al. ........ | 128/653.1 |
| 5,257,636 A | 11/1993 | White ........................ | 128/897 |
| 5,316,024 A | 5/1994 | Hirschi et al. ............... | 128/899 |
| 5,425,367 A | 6/1995 | Shapiro et al. ........... | 128/653.1 |
| 5,425,382 A | 6/1995 | Golden et al. ............... | 128/899 |
| 5,645,065 A | 7/1997 | Shapiro et al. ........... | 128/653.1 |
| 5,649,546 A | 7/1997 | Steinbeck .................... | 128/737 |
| 5,669,383 A | 9/1997 | Johnson ...................... | 128/657 |
| 5,782,765 A | 7/1998 | Jonkman ..................... | 600/424 |
| 5,879,297 A | 3/1999 | Haynor et al. .............. | 600/407 |
| 5,902,238 A * | 5/1999 | Golden et al. ............... | 600/424 |
| 5,928,248 A | 7/1999 | Acker .......................... | 606/108 |
| 6,059,718 A * | 5/2000 | Taniguchi et al. ........... | 600/117 |
| 6,076,007 A | 6/2000 | England et al. ............. | 600/424 |
| 6,119,033 A | 9/2000 | Spigelman et al. ........... | 600/426 |
| 6,129,668 A * | 10/2000 | Haynor et al. .............. | 600/424 |
| 6,138,681 A * | 10/2000 | Chen et al. .................... | 128/899 |
| 6,173,715 B1 | 1/2001 | Sinanan et al. .............. | 128/899 |
| 6,263,230 B1 * | 7/2001 | Haynor et al. .............. | 600/424 |
| 6,360,615 B1 * | 3/2002 | Smela .................... | 73/862.474 |
| 6,363,940 B1 * | 4/2002 | Krag .......................... | 128/899 |

(Continued)

*Primary Examiner*—Van T. Trieu
(74) *Attorney, Agent, or Firm*—Downs Rachlin Martin PLLC

(57) ABSTRACT

An apparatus for locating a magnet and/or determining the orientation of the apparatus relative to the magnet. In one embodiment, the apparatus includes a multi-axis magnetic field sensor movable in a reciprocating manner so as to permit sensor readings at multiple spaced locations. In another embodiment, the apparatus includes a plurality of multi-axis magnetic field sensors arrayed along a straight line. The apparatus may be used in a number of medical and other applications, including tissue resection, tracking movement of a medical device in a body cavity and tracking movement of an internal organ.

6 Claims, 4 Drawing Sheets

U.S. PATENT DOCUMENTS

| | | | |
|---|---|---|---|
| 6,401,722 B1 | 6/2002 | Krag | 128/898 |
| 6,453,190 B1 | 9/2002 | Acker et al. | 600/424 |
| 6,505,062 B1 | 1/2003 | Ritter et al. | 600/407 |
| 6,698,433 B2 | 3/2004 | Krag | 128/899 |
| 6,755,199 B2 | 6/2004 | Rehder et al. | 128/899 |
| 6,775,404 B1 | 8/2004 | Pagoulatos et al. | 382/154 |
| 6,812,842 B2 | 11/2004 | Dimmer | 340/572.4 |
| 6,822,570 B2 | 11/2004 | Dimmer et al. | 340/572.1 |
| 6,838,990 B2 | 1/2005 | Dimmer | 340/572.4 |
| 6,889,833 B2 | 5/2005 | Seiler et al. | 206/370 |
| 6,895,267 B2 * | 5/2005 | Panescu et al. | 600/424 |
| 6,977,504 B2 | 12/2005 | Wright et al. | 324/326 |
| 2004/0143182 A1 | 7/2004 | Kucera et al. | |
| 2004/0143183 A1 | 7/2004 | Toyoda et al. | 600/424 |

* cited by examiner

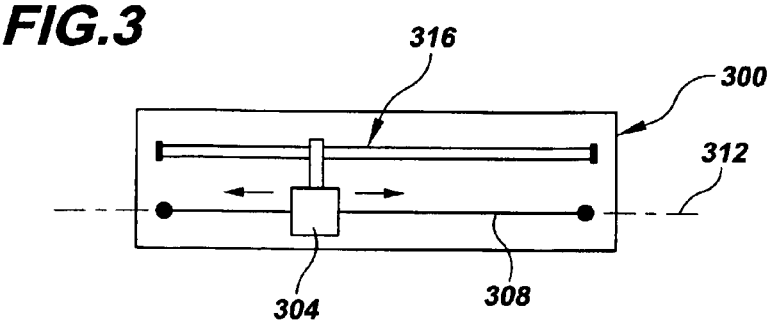
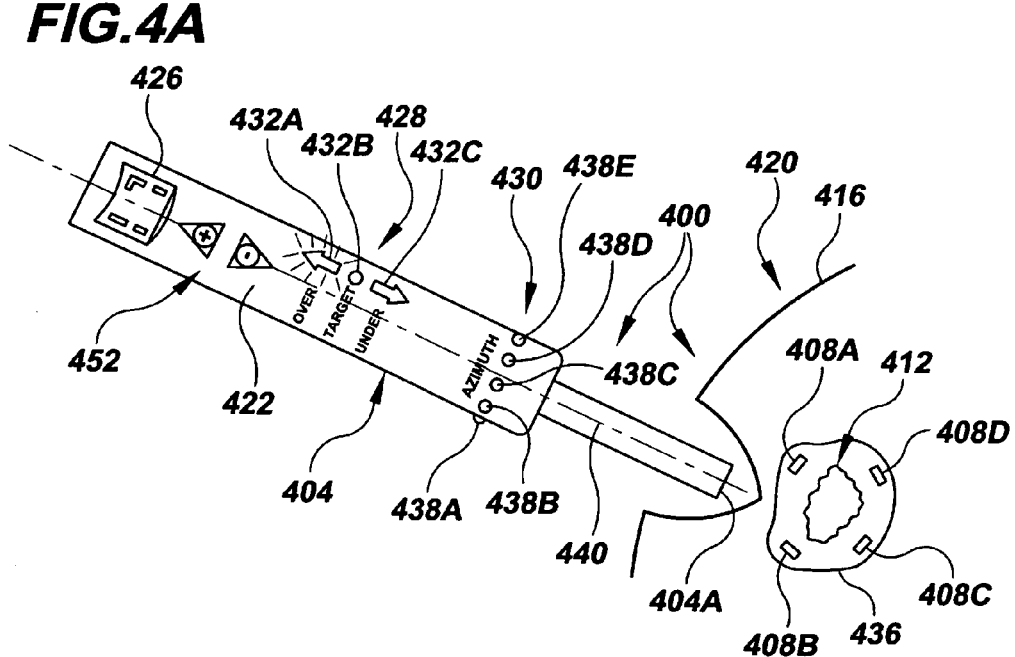
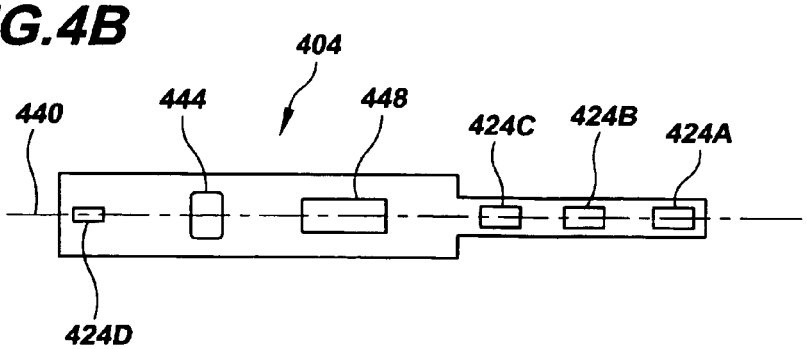

MAGNET LOCATING APPARATUS AND METHOD OF LOCATING A MAGNET USING SUCH APPARATUS

RELATED APPLICATION DATA

This application claims the benefit of priority of U.S. Provisional Patent Application Ser. No. 60/673,558, filed Apr. 20, 2005, and titled "Magnetic Marker Locating Techniques And Probe," that is incorporated by reference herein in its entirety.

FIELD OF THE INVENTION

The present invention generally relates to the field of remote sensing and localization. In particular, the present invention is directed to a magnet locating apparatus and method of locating a magnet using such apparatus.

BACKGROUND

Many diagnostic and surgical procedures utilizing indwelling medical devices require that the location of one or more fiducial markers or part(s) of an indwelling medical device be known with accuracy for the medical procedure to be properly performed and be successful. An example of the use of fiducial markers in a surgical context is the bracketing of a tissue volume containing a tissue mass, e.g., a non-palpable lesion, to be excised. Examples of this sort of tissue bracketing are disclosed in quite some detail in U.S. Pat. No. 6,698,433 to Dr. Krag, titled "System And Method For Bracketing And Removing Tissue," which is incorporated herein by reference in its entirety. Tools for performing the bracketing method disclosed in Dr. Krag's patent include a locating device for locating each fiducial marker implanted prior to surgery. In order to locate the fiducial markers, the locating device must be as accurate as possible.

In Dr. Krag's tissue bracketing method, as well as in other in vivo methods utilizing fiducial markers, it is typically desired that the fiducial markers be as unobtrusive as practicable, while at the same time providing the necessary locational accuracy. Some conventional fiducial markers may be called "active" markers based on their direct excitation by electricity supplied to the markers via wires extending from the markers. Other conventional fiducial markers may be called "passive" markers in that they are not excited via hard-wiring, but rather are excited by radio frequency (RF) electromagnetic energy, emitted by a suitable transmitter. The fiducial markers utilized in Dr. Krag's tissue bracketing procedure are passive markers that contain resonance circuitry that responds to particular RF electromagnetic energy from the transmitter.

While these wired and resonant-type markers provide good locational accuracy, each has its drawback. An obvious drawback of wired markers is the presence of the wires, which can be obtrusive in many situations. A drawback of both wired and resonant-type markers is their microcircuitry, which makes the markers relatively complex and may require that the markers be larger than desirable. In addition, both types of markers require external energy sources that further add to the complexity of the systems utilizing such markers. It is highly desirable, therefore, that fiducial markers used for medical purposes be simple and capable of operating without any external energy source. This simplicity can translate into less complex systems for supporting the use of such markers.

SUMMARY

In one aspect, the present invention includes an apparatus for locating a margin located within a body an offset distance from a magnetic marker located in the body and having a magnetic field. The apparatus comprise a body having a reference point positionable at the margin. At least one magnetic field sensor is configured to generate an output signal as a function of the magnetic field of the magnetic marker. A selector is provided for presetting the offset distance between the margin and the magnetic marker. A central processor is configured to calculate a location of the margin relative to the reference point as a function of the output signal and the offset distance. A display is operatively coupled to the central processor and configured to display information about the location.

In another aspect, the present invention includes an apparatus for determining the location of at least one fiducial marker emitting. The apparatus comprises at least one magnetic field sensor having a sensor reference axis. A sound generator configured to generate a first sound that aurally indicates orientation of the sensor reference axis with respect to the fiducial marker.

In yet another aspect, the present invention includes an apparatus for locating a magnet having a magnetic field. The apparatus comprises a body having a sensor axis. A magnetic field sensor is configured to sense the magnetic field of the magnet. The magnetic field sensor is movably engaged with the body so as to be reciprocatingly movable along the sensor axis so as to provide multiple sampling points. An actuator is provided for moving the magnetic field sensor in a reciprocating manner along the sensor axis during use of the magnetic probe.

In a further aspect, the present invention includes a method of determining the location of a magnet using a plurality of magnetic field sensors. The method comprises determining whether any one or more of the plurality of magnetic field sensors has saturated and calculating the location of the magnet using only |ones| of the plurality of magnetic field sensors that are not saturated.

In yet a further aspect, the present invention includes a method of determining the location of a magnet in an environment having an ambient magnetic field. The magnet emits a first magnetic field distinct from the ambient magnetic field. The method comprises providing a magnet locating apparatus comprising at least one magnetic field sensor. The ambient magnetic field is sensed at a plurality of locations via the at least one magnetic field sensor so as to generate a plurality of first sensed values. A plurality of ambient magnetic field gradient values are determined as a function of the plurality of first sensed values so as to account for non-uniformity in the ambient magnetic field.

In still a further aspect, the present invention includes a method of minimizing the effects of sensor drift caused by temperature and other effects. The method comprises providing a magnet locating device configured to locate magnet. |The magnet locating device includes a sensor array having a plurality of magnetic field sensors each having associated therewith at least one calibration constant. One of the plurality of magnetic field sensors is a reference sensor. Substantially immediately prior to using the magnet locating device, the at least one calibration constant of each of said plurality of magnetic field sensors except the at least one calibration constant associated with the reference sensor is adjusted so as to yield the most consistent possible agreements in the readings of the plurality of magnetic field sensors.|

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein:

FIG. 3 is a high-level schematic diagram of an alternative magnet locating apparatus of the present invention having a single moving magnetic field sensor;

FIG. 4A is a partial elevational view of a self-contained handheld magnet locating probe of the present invention and a patient; FIG. 4B is a high-level schematic diagram of electronics located inside the probe of FIG. 4A;

DETAILED DESCRIPTION

Figure 1:
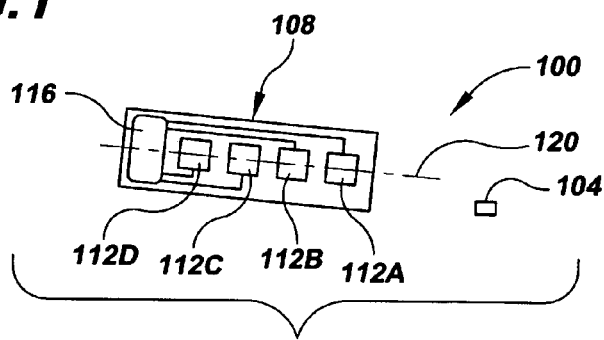
FIG. 1 is a high-level schematic diagram of a magnetic locational system of the present invention that includes at least one magnet and a magnet locating apparatus.

Referring now to the drawings, FIG. 1 illustrates a basic magnetic locational system 100 of the present invention. At a high level, system 100 includes a magnet 104 and a magnet locating apparatus 108. As discussed below in more detail, magnet 104 may function as a fiducial marker, e.g., in the manner of the bracketing markers disclosed in the Krag patent discussed in the Background section above, or as a reference fixedly attached to an indwelling medical device, such as a catheter, probe or targeted therapy delivery device, or to an internal organ, or suspended in a freely moving stream within the body such as the blood or gastrointestinal tract among other things. As also discussed below in detail, magnet locating apparatus 108 may be a movable probe, such as a handheld probe, for detecting magnet 104 typically when it is fixed or, alternatively, may be a fixed detector typically, though not necessarily, for detecting magnet 104 when it is moving.

Magnet 104 may be any type of magnet, such as a permanent magnet, e.g., a rare-earth magnet, samarium-cobalt magnet, ceramic magnet, plastic magnet or alnico magnet, among others, or an electromagnet. The suitability of these various types of magnets for various applications of magnet 104 will be readily understood by those skilled in the art, such that it is not necessary to present further details regarding the types of magnets that may be used in the present invention. Utilizing magnets, such as magnet 104, as fiducial markers has the benefits of being extremely simple (they are generally just masses of magnetic material), not requiring wires or other tethers to external equipment, not requiring complex resonant circuitry and not requiring external excitation sources. In addition, certain magnets, such as rare-earth magnets, produce high magnetic field intensities that, in turn, enable the use of small magnets. In addition, magnets are typically low cost and can readily be made in a wide variety of shapes.

Magnet locating apparatus 108, on the other hand, may include any one or more of a number of unique features that set it apart from conventional magnet locating devices. Generally, apparatus 108 includes a plurality of magnetic field sensors (for the sake of illustration, FIG. 1 shows four magnetic field sensors 112A-D) and a processor 116 in operative communication with the sensors. As those skilled in the art will appreciate, processor 116 may be, e.g., a microprocessor, application specific integrated circuit, etc., that runs software, or, alternatively, hardware-only computational circuitry or a combination of the two. Each magnetic field sensor 112A-D senses the magnetic field at its location and generates one or more (depending upon the number of sensing channels present) signals as a function of the sensed field strength. Typically, though not necessarily, each sensor 112A-D is a three-orthogonal-axis sensor that senses field strength along each of local x, y and z axes.

Processor 116 performs various algorithms, such as the locating and calibrating algorithms described below, for determining the position of magnet 104 relative to apparatus 108 as a function of the signals from sensors 112A-D and for providing other functionality, such as determining the orientation of the apparatus relative to the magnet, among other things. It is noted that sensors 112A-D may be affixed to a circuit board (not shown) or attached to other suitable structures. In addition, if magnetic field sensors 112A-D are small enough, they may be integrated into a system-on-chip along with processor 116. The unique and other features of magnet locating apparatus 108 are described below in detail.

Locating and Calibrating Algorithms

As mentioned, processor 116 of magnet locating apparatus 108 performs various algorithms for determining the location of magnet 104. An example of particular algorithms the present inventors have found particularly suitable for applications such as tissue bracketing are described below. Of course, those skilled in the art will readily appreciate that a magnetic locating apparatus of the present invention, such as apparatus 108 of FIG. 1, may utilize algorithms other than the algorithms detailed herein.

Basic Theory

|The magnetic field $\vec{B}$, measured at an origin, caused by a small bar magnet having magnetization $\vec{m}$ located at $\vec{r}$ is accurately given by modeling the magnet as a dipole (in this and subsequent expressions, a vector quantity is indicated by the presence of an arrow (→) over the corresponding variable):

$$\vec{B} = \left( \frac{(3\vec{m} \cdot \vec{r})\vec{r}}{r^5} - \frac{\vec{m}}{r^3} \right) \quad \{1\}$$

Therefore, the field that would theoretically be measured by an error-free sensor located at x is given by:

$$\vec{B}^{theo} = \left( \frac{[3\vec{m} \cdot (\vec{r} - \vec{x})](\vec{r} - \vec{x})}{|(\vec{r} - \vec{x})|^5} - \frac{\vec{m}}{|(\vec{r} - \vec{x})|^3} \right) + \vec{B}_{amb} \quad \{2\}$$

where $\vec{B}_{amb}$ is the value of the ambient field (Earth's field plus any local disturbances). It is normally assumed that the ambient field varies linearly with position so that its value at a specific location $\vec{x}$ is given by:

$$\vec{B}_{amb} = \vec{B}_{amb}{}^o + \nabla \vec{B} \cdot \vec{x}$$

where $\nabla \vec{B}$ are the (assumed constant) components of the ambient field gradients and $\vec{B}_{amb}{}^o$ is the ambient field strength at $\vec{x} = \vec{0}$. Measurements in operating theaters have clearly established that the ambient field can be significantly non-uniform, so minimizing the effects of field gradients by the design of magnet locating apparatus 108 or explicitly accounting for the gradients in the solution algorithm is important in many cases if the localization technique is to be accurate at relatively long distances. When this consideration is employed in apparatus 108, it typically affects several of its design features.

Formulation of Inverse Algorithm

Consider an array of fixed magnetic field sensors arrayed in a straight line, such as sensors 112A-D are arrayed along sensor array, or sensor reference, axis 120. Adopting a coordinate system in which the sensor at the front of apparatus 108, sensor 112A in FIG. 1, is located at the origin and the other sensors, i.e., sensors 112B-D, are arranged along the y-axis. If it is desired to locate magnet 104, there are a total of twelve unknowns, namely:

1. the three components of the magnetization vector $\vec{m}$;
2. the three components of the magnet position vector $\vec{r}$;
3. the three components of the ambient field $\vec{B}_{amb}{}^o$ measured at x=0; and
4. the three terms that describe the gradient in the ambient field down the axis of the probe, namely $$\frac{\partial B_x}{\partial y}, \frac{\partial B_y}{\partial y} \text{ and } \frac{\partial B_z}{\partial y}.$$

Some previous work in this area has ignored the effects of gradients in the ambient field and relied on placement of the magnetic field sensors in a specified nonlinear, planar fashion. This can have advantages when gradients are small. However, in the case of large gradients, it can be beneficial to arrange the sensors along a straight line, e.g., in the manner of sensors 112A-D of FIG. 1 in order to effectively reduce the number of unknown gradients to three for environments in which the gradients must be computed. In the context of magnet locating apparatus 108 being a handheld probe, a linear array of sensors 112A-D can also result in a relatively slim probe that is easily manipulated by a surgeon and that can be inserted into an incision if necessary. Such a handheld probe is illustrated below in each of FIGS. 4A and 5.

For less demanding applications in which the ambient field is relatively uniform and gradients can be safely ignored (or estimated through the use of additional magnetic field sensors), increased localization distance may be achieved by adopting an array geometry that is not one-dimensional. For example, an L-shaped or "zig-zag" geometry can be advantageous since this configuration reduces the distance between the farthest sensor and the magnet while enabling the front of the probe to remain sufficiently narrow to be inserted in an incision. |However, the potentially improved accuracy offered by such an arrangement in a gradient-free environment (assuming this can be assured) is not compelling in applications in which the magnet locating apparatus can be readily oriented so that it is directly facing the magnet. Such an orientation provides the maximum effective gradiometer baseline length and good accuracy despite the linear arrangement|.

Sensors are commercially available to measure one, two or all three axes of a magnetic field. If three-axis sensors are employed, these twelve unknown quantities can be solved for by using four or more sensors, since each sensor contributes three pieces of information (i.e., the three orthogonal field components). Solving for the 12 unknown quantities in terms of the field components measured by the sensors, may be accomplished by minimizing a figure-of-merit, e.g.:

$$J = \sum_{\text{sensor } j} \sum_{\text{component } i} (B_{ij} - B_{ij}^{theo})^2 \quad \{4\}$$

where $B_{ij}$ is the field measured at sensor j along axis i, and $B_{ij}^{theo}$ is the value calculated by Equation 1, given assumed values for the 12 unknown quantities.

Improved accuracy can be obtained in applications that allow the magnitude m of the magnetization of magnet 104 to be predetermined through measurement or published specifications. For example, a fixture (not shown) can be attached to magnet locating apparatus 108 that puts magnet 104 into a known position just before it is used. A simple algorithm based on Equation {2} can then be used to derive the magnitude of the magnetization from the measured fields. When m is known, it may be input to the algorithm so that one need only solve for the two angles that define the orientation of magnet 104 in space.

Inverse Problem Solution Algorithm

The figure-of-merit, i.e., J of Equation {4}, may be minimized using an appropriate minimization technique, e.g., the Levenberg-Marquardt algorithm. The Levenberg-Marquardt algorithm is an iterative technique that requires an initial guess for the various unknowns. When magnet locating apparatus 108 is a handheld probe, one could ordinarily use the last computed position of magnet 104, since the solution algorithm is sufficiently fast to keep up with typical probe velocities caused by hand motion. To initialize the very first calculation, or to "regain lock" if apparatus 108 is moved beyond range and then returned to within range, new initial guesses are needed. The present inventors have found using the algorithms disclosed herein that the initial guesses need not be very accurate since the marker can always be assumed to be generally in front of the probe. Excellent results have been obtained by assuming for the initial guess that magnet 104 is located along sensor array axis 120 at a distance given by:

$$y_{magnet} = \frac{2m}{\sqrt{\sum_{component\ i}(B_{i1} - B_{in})^2}} \quad \{5\}$$

It is noted that Equation 5 utilizes the convention that the magnetic field sensors, e.g., sensors 112A-D of FIG. 1, are numbered sequentially from the "front" of the magnet sensing apparatus, e.g., apparatus 108, i.e., the portion of the apparatus that points toward the magnet under consideration, e.g., magnet 104, during normal locating procedures, with n being the number of the sensor farthest from the front, in the case of apparatus 108, sensor 112D. The other initial guesses are currently obtained by assuming that the ambient field has a zero gradient and component values are equal to the fields measured by the last ($n^{th}$) sensor. If the magnitude m is accurately known and is input to the algorithm, the initial guesses for the two angles that define the orientation of the marker can be arbitrarily assigned.

Sensor Calibration

Generally, use of a very small magnet for magnet 104 is highly desirable for ease of insertion into the region of interest of a patient and for accuracy in defining a specific position of the magnet. The fields given by such small magnets (even when they are of the rare earth type) are generally much smaller than the ambient Earth's field, especially for sensors located relatively distant from the front of the apparatus and, thus, far from the magnet. In such cases, the sensors must be highly accurate. To achieve this accuracy, an improved estimate may be calculated for the magnetic field $\vec{B}^{cal}$ given in terms of the raw readings $\vec{B}^{raw}$ using:

$$\vec{B}^{cal} = \vec{A}\,\vec{B}^{raw} + \vec{B}^{o} \quad \{6\}$$

For three-axis sensors, $\vec{A}$ is a 3×3 matrix of calibration constants and $\vec{B}^o$ is a set of three constant offsets. These values are obtained individually for each sensor by placing the sensor at a known orientation in an arbitrary coordinate system. The components of the Earth's field measured by the sensor are recorded, and then the values of calibration constants and offsets that will minimize the difference between the measured and theoretically calculated fields are then calculated. This may be done once during probe manufacture using a dedicated calibration fixture. The use of a full 3×3 matrix (rather than individual gain constants for each axis) allows this procedure to compensate for sensor misalignment on the circuit board, misalignment within the sensor chip itself, and so-called "cross-axis" effects.

The calibration constants $\vec{A}$ and $\vec{B}^o$ have been observed to change slightly over time due to such effects as changes in sensor temperature. Some applications may demand the highest level of accuracy. In this case, it may be necessary to recalibrate the sensors immediately prior to use. However, a full re-calibration of the sensors before each use is inconvenient. Instead, a simpler procedure can be used to restore the self-consistency of the sensors. A self-consistent calibration procedure (rather than a recalibration in an absolute sense) can be sufficient to ensure accuracy, since the inverse solution algorithm discussed above relies on determining the magnet position that manifests itself as observed differences in field strength between sensors. Thus, for example, if the ambient gradient is small, it is required only that there be little or no difference in field readings if no magnet is present.

With this in mind, a quick "recalibration" can be performed before use by slowly moving the magnetic locating apparatus, e.g., apparatus 108, in a region located away from metal objects and magnets that could give rise to steep gradients in the ambient field. The apparatus is moved over a range of orientations, e.g., angles that sensor array axis 120 makes relative to a straight line 124 radiating from magnet 104, that roughly encompasses those that can be anticipated during use. For example, the apparatus is unlikely to be oriented so that it is pointing away from the patient and such orientations need not be used. The field measurements from each sensor are recorded as it is moved. For a magnet locating apparatus containing n sensors, the calibration constants for the n−1 sensors furthest from the front of the apparatus are then adjusted to minimize the differences in recorded fields between those sensors and the fields measured by the first sensor over the entire range of motion. The corrected values of the first sensor's fields are obtained using the initial calibration values determined during the full calibration $\vec{A}$ and $\vec{B}^o$ for that sensor.

Procedure for Detecting a Gradient in the Ambient Field

An analogous procedure can be employed prior to use to determine whether the gradient compensation procedure discussed in the Formulation of Inverse Algorithm section above should be used in a particular operating environment. As discussed previously, when the ambient field is not uniform and the magnetic field sensors are arranged along a sensor array axis, e.g., as sensors 112A-D are arranged along sensor array axis 120, improved accuracy is obtained by explicitly solving for the ambient field gradient down the sensor array axis. However, in more favorable environments where the gradient in ambient field is small, improved accuracy is obtained by assuming a zero gradient. In the latter case, some of the sensors may be redundant. Magnetic field measurements from the redundant sensors can be used to improve accuracy. To determine whether a gradient should be assumed to exist when solving the inverse problem, the magnet locating apparatus can be placed in the region where it will be used before any magnetic markers are introduced into this region. The calibrated fields along each sensor axis may then be fitted to a straight line, and the value of the slope may be compared to a criterion previously developed from numerical simulations. If the absolute value of the slope is greater than this criterion, the full version of the algorithm discussed in the Formulation of Inverse Algorithm section should be used during the actual locating of the magnet. Otherwise, the gradient may be assumed to be zero.

Compensation for Sensor Saturation

Most magnetic field sensors saturate at sufficiently high field strengths and, consequently, return inaccurate readings. When the one or more magnets, e.g., magnet 104, each have a relatively weak magnetic field, this is generally a problem only for the sensor closest to the magnet, e.g., sensor 112A in apparatus 108. It is desirable, though not essential, to compensate for this effect without incurring the expense and size penalty of providing one or more additional sensors of different types, e.g., Hall-type sensors, that saturate at higher field strength but are less accurate than other types. To do this, the inverse problem may be reformulated in a way that ignores the field readings for the sensors reporting field strengths greater than a prescribed maximum value. For example, in the four-sensor design of magnet locating apparatus 108, if the y-axes of first and second sensors 112A-B become saturated, the inverse problem can be formulated using the x- and z-axes channels of sensors 112A-B and all three axes channels of sensors 112C-D.

For a given set of unsaturated sensor channels, it may be possible to obtain a full solution, including the calculation of the gradient, even if some channels are ignored because of saturation. However, if there are not enough unsaturated channels to perform a full solution, a valid solution can still be obtained by assuming the ambient field gradient is negligible, thereby reducing the number of unknown quantities that must be calculated. Ignoring gradients in the ambient field is generally valid where saturation is a problem close to the magnet, since in that region the gradient in the measured field is dominated by the effects of the magnet and the ambient field may be regarded as effectively constant.

Demonstration Calculation

If a magnet locating apparatus of the present invention, such as apparatus 108, utilizes the algorithms discussed above, it estimates the location of a magnet, e.g., magnet 104, by measuring the magnetic field created by the magnet at various locations. The strength of the magnetic field of the magnet is typically much smaller than the strength of the ambient earth's field, so special care must be taken when the ambient field is not spatially constant. Following is a demonstration calculation of how the position of the magnet can be calculated from its field. This calculation demonstrates the importance of accounting for spatial gradients in the ambient field.

The magnet localization algorithm and the effects of gradients in the ambient field can be readily demonstrated using a computer spreadsheet application, such as the EXCEL® spreadsheet application available from Microsoft Corporation, Redmond, Wash. In the following example, the sensor array axis, e.g., sensor array axis 120 of FIG. 1, is taken to coincide with the y-direction of a mutually orthogonal coordinate system fixed to the apparatus. It is assumed that the magnet is located at an (x,y,z) position (−10, 50, 10), wherein these parenthetical distances are measured in millimeters. This position is typical of clinical use: the magnet is generally in front of the apparatus but is slightly displaced to the side relative to the sensor array axis. The distance from the apparatus to the magnet is also a fairly typical value of just over 50 mm. Of course, in practice the position of the magnet, the ambient field and the other parameters in the calculation will vary.

The orientation of the magnet is not normally known, but the total magnetization is a known value since it can be measured before the magnet is used. For a small Nd—Fe—Bo magnet, the total magnetization has a value of about $4\pi \times 10^4$ Gauss-mm$^3$ (expressing the magnetization in terms of $4\pi$ is convenient since this normalization constant is used in CGS units). Thus, individual components of the magnetization vector $\vec{m}$ in this example can be arbitrarily assigned as $4\pi \times 10^4$ (−0.3, 0.77, 0.7)mm. Again, vector quantities are denoted by an arrow appearing above a variable.

While a typical value for the magnitude of the ambient field measured at the location of the sensor closest to the magnet will be approximately 500 milliGauss (mG), the direction of the ambient field, measured in a coordinate system fixed to the apparatus, will depend on the orientation of the apparatus.

The ambient field vector $\vec{B}_{amb}^{\,o}$ is taken to be 500 mG (0.4, 0.45, 0.8) mm in this demonstration. Finally, it is assumed here that a gradient exists in the ambient field along the direction of the sensor array axis. Measurements taken in operating theaters at prototypical locations indicate that gradients on the order of 1.5 mG/mm are often present. Based on this, it is assumed that the directional derivative of the ambient field along the y-axis, ŷ, is:

$$\nabla \vec{B}_{amb} \cdot \hat{y} = (0.8, -1.5, 1.2) \text{mG/mm}. \quad \{7\}$$

The three components of this vector correspond to the derivatives of the three components of the ambient field with respect to y. A typical linear sensor geometry used in testing has sensors spaced at 20 mm intervals, and it is assumed here that the four sensors' coordinates $y_{sensor}$ are 0, −20, −40, and −60 mm.

Given this information, it is a relatively simple matter to calculate the actual value of the magnetic field at each sensor by approximating the magnet as a dipole using Equation {2}. In this expression, the magnet is located at position $\vec{r}$ and the sensor is located at $\vec{x}$. The ambient field is assumed to vary linearly along the sensor array axis, so that at any sensor location $y_{sensor}$:

$$\vec{B}_{amb} = \vec{B}_{amb}^{\,o} + (\nabla \vec{B} \cdot \hat{y}) y_{sensor} \quad \{8\}$$

Here, $\vec{B}_{amb}^{\,o}$ is simply the value of the ambient field at y=0, the position of the first sensor.

To calculate the position of the magnet from the field values measured at each sensor, the assumed values are varied for the unknown quantities until the measured field values best match those predicted for a magnet. The unknowns that are varied in such a calculation are the various quantities listed above, namely, the magnet's location and orientation, the ambient field strength, and the values of the gradients in the ambient field. For demonstration purposes, such a calculation can be conveniently performed using the "Solver" function of the EXCEL® spreadsheet application to minimize the sum of the squares of the differences between the calculated fields and those measured at the sensors:

$$J = \sum_{sensor\ j} \sum_{component\ i} (B_{ij} - B_{ij}^{actual})^2 \quad \{9\}$$

Here, $B_{ij}$ is the measured (or actual) value of the $i^{th}$ component of the magnetic field at the $j^{th}$ sensor.

The demonstration calculation was performed in two ways. In the first calculation, gradients in the ambient field were recognized to exist, and the values of its components were varied along with the other unknown quantities until the figure-of-merit J was minimized. The second calculation was the same except that the gradients in the ambient magnetic field were neglected. Errors in the magnetic field sensor readings are ignored in both calculations. The results are shown immediately below in Tables IA-B and IIA-B, respectively.

TABLE IA

Sensor Readings—Gradients Considered

| Sensor | "Actual" Field Values (mG) | | | "Converged" Field Values (mG) | | |
|---|---|---|---|---|---|---|
| | x | y | z | x | y | z |
| 1 | 185.5495 | 352.9801 | 381.4402 | 185.5488 | 352.9773 | 381.4448 |
| 2 | 182.6982 | 300.857 | 364.5861 | 182.721 | 300.8465 | 364.5645 |
| 3 | 168.4848 | 305.2495 | 345.3906 | 168.4513 | 305.2636 | 345.42 |
| 4 | 152.6501 | 325.0079 | 323.9549 | 152.6658 | 325.0014 | 323.9429 |

TABLE IB

Calculated Values—Gradients Considered

| Quantity | "Actual" Values | | | "Converged" Values | | |
|---|---|---|---|---|---|---|
| | x | y | z | x | y | z |
| Position, mm | −10 | 50 | 10 | −10.66 | 49.58 | 10.51 |
| Gradient, mG/mm | 0.8 | −1.5 | 1.2 | 0.79 | −1.49 | 1.21 |
| Ambient, mG | 200 | 223 | 400 | 199.2 | 223.8 | 400.7 |
| Magnetization | −3006 | 6931 | 7637 | −3363 | 6507 | 7858 |

TABLE IIA

Sensor Readings—Gradients Considered

| Sensor | "Actual" Field Values (mG) | | | "Converged" Field Values (mG) | | |
|---|---|---|---|---|---|---|
| | x | y | z | x | y | z |
| 1 | 185.5495 | 352.9801 | 381.4402 | 185.5507 | 347.5043 | 382.7092 |
| 2 | 182.6982 | 300.857 | 364.5861 | 182.2687 | 313.2929 | 369.2399 |
| 3 | 168.4848 | 305.2495 | 345.3906 | 168.7158 | 307.4545 | 340.8905 |
| 4 | 152.6501 | 325.0079 | 323.9549 | 152.8467 | 315.8426 | 322.5316 |

TABLE IIB

Calculated Values—Gradients Considered

| Quantity | "Actual" Values | | | "Converged" Values | | |
|---|---|---|---|---|---|---|
| | x | y | z | x | y | z |
| Position, mm | −10 | 50 | 10 | −45.8 | 0.4 | −35.4 |
| Gradient, mG/mm | 0.8 | −1.5 | 1.2 | N/A | N/A | N/A |
| Ambient, mG | 200 | 223 | 400 | 152.8 | 336.9 | 305.6 |
| Magnetization | −3006 | 6931 | 7637 | −10416 | −2220 | 1408 |

In the first case, wherein gradients are included in the calculation, i.e., the case reflected in Tables IA and IB above, the total position error is less than 1 mm, and all the various unknown quantities are estimated fairly accurately.

In the second case, wherein the gradients are neglected, i.e., the case reflected in Tables IIA and IIB above, the total position error is very large. The converged field values are reasonably close to the actual field values, implying that the inverse solution was performed correctly. However, because gradients were neglected, the algorithm makes a large error in magnet position in order to minimize the difference between the actual and calculated field values. In other words, the errors caused by neglecting the gradients are compensated by erroneously positioning the magnet.

The ambient magnetic field cannot be expected to be spatially constant when substantial metallic objects are present. Indeed, the present inventors have measured magnetic field gradients on the order of 1.5 mG/mm in operating theaters. The effects of such gradients must be minimized for accurate locating of small magnetic markers. This may be accomplished, e.g., by using a linear probe of relatively small dimensions, explicitly calculating the values of the ambient field gradients during operation, or both.

The example described above assumes that field gradients are linear and only exist along the sensor axis of the magnet locating apparatus. This is a reasonable assumption if the magnetic field sensors are arranged in a linear fashion and the apparatus is kept relatively short. However, the same technique can be readily extended to account for linear gradients in multiple dimensions or for a nonlinear dependence of the ambient field on position. Estimation of nonlinear or multi-dimensional gradients will introduce additional unknowns and require the use of additional sensors. As a practical matter, accuracy and sensitivity limits of current magnetic field sensors could make estimation of higher order terms difficult.

Probe Geometry Considerations

The positions and arrangements of the magnetic field sensors within the magnet locating apparatus are important design considerations. If the sensors are spaced too closely together, their readings will not differ enough from each other to allow an accurate calculation of the unknown quantities. However, if the sensors are placed too far apart, in a linear arrangement the last two sensors (sensors n and n−1, in FIG. 1, sensors 112C-D) may be so far from the magnet that the marker's field is overwhelmed by the ambient field. In this case, the readings of the last two sensors (sensors 112C-D in FIG. 1) may not differ by more than the sensor error or the gradient in the ambient field, rendering an accurate solution infeasible. Also, as the total distance between the first and last sensors (sensors 112A and 112D in FIG. 1) increases, the ambient field may no longer be accurately represented by the linear function of Equation {3}, above.

For relatively short distances between the first and last magnetic field sensors, uniform sensor spacing yields reasonable results. However, improved accuracy can be obtained by locating the sensors at the front of the apparatus, e.g., sensors 112A-B, closer together than the sensors at the back, e.g., sensors 112C-D. This yields better performance since the overall distance between the first and last sensors can be reduced, which, in turn, reduces the effect of ambient field gradients. The relative accuracy of the readings of the sensors at the front of the apparatus, e.g., sensors 112A-B, is not compromised by placing them closer together, since the field from the magnet varies more rapidly with distance the closer one is to the magnet.

As mentioned previously, two- and three-dimensional sensor arrangements offer improved accuracy, e.g., if the ambient field is relatively uniform and if the magnet is to be placed in arbitrary positions relative to the probe. The one-dimensional arrangement discussed above is sufficient and, in fact, desirable in applications where the magnet locating apparatus, e.g., apparatus 108 of FIG. 1, can be freely oriented so that it is facing the magnet, e.g., magnet 104, especially when the ambient field is not spatially uniform. Such an orientation provides the maximum gradiometer baseline length in a linear apparatus.

Figure 2A:
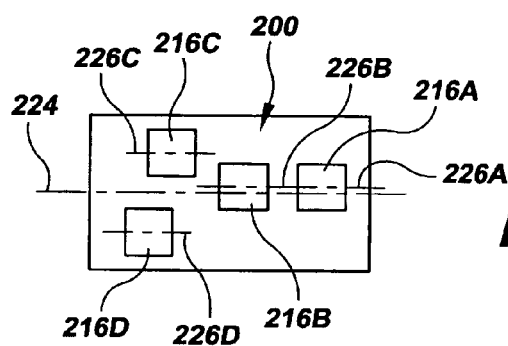
FIG. 2A is a schematic diagram of an alternative arrangement of magnetic field sensors that may be used in a magnet locating apparatus of the present invention.
Figure 2C:
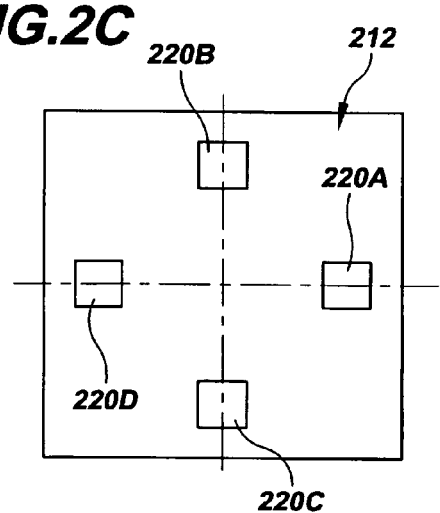
FIG. 2C is a schematic diagram of yet another alternative arrangement of magnetic field sensors that may be used in a magnet locating apparatus of the present invention.
Figure 2B:
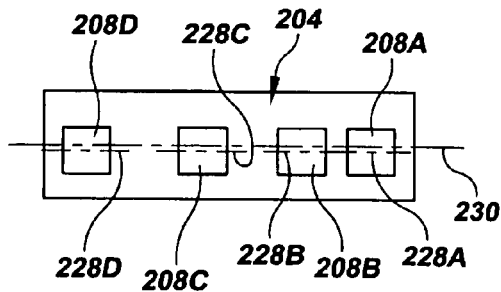
FIG. 2B is a schematic diagram of another alternative arrangement of magnetic field sensors that may be used in a magnet locating apparatus of the present invention.

FIGS. 2A-C illustrate, respectively, a non-linear sensor arrangement 200, a linear arrangement 204 in which the spacing between adjacent magnetic field sensors 208A-D is non-uniform and a non-linear (two-dimensional) arrangement 212, each of which may be used in place of the linear, evenly spaced sensor arrangement illustrated in FIG. 1 when design conditions are suitable for these alternative arrangements. It is noted that for each of these arrangements 200, 204, 212 the corresponding sensors 208A-D, 216A-D, 220A-D are assumed to lie in a plane to facilitate mounting on a printed circuit board or be incorporated into a system-on-chip, as practicable. However, such planar arrangements are not required, and there may be applications that would benefit from mounting one or more sensors on one or more different planes.

In FIG. 2A, four multi-axis magnetic field sensors 216A-D are arranged in non-linear configuration 200 along a sensor array axis 224. Two of sensors, i.e., 216A-B are located so that one central axis 226A-B of each coincides with sensor array axis 224. However, the other two sensors, i.e., sensors 216C-D, are located so that a central axis 226C-D of each is spaced from sensor array axis 224 and central axes 226C-D are located on opposite sides of the sensor array axis. Arrangement 200 is an example of the "zig-zag" configuration mentioned in the Formulation of Inverse Algorithm section above and can be advantageous because all of sensors 216A-D can be located closer to a magnet than in a simple linear arrangement, and it permits sampling of off-axis fields. Arrangement 200 provides an additional degree of freedom that can be useful in designing a magnet locating apparatus of the present invention. In a handheld magnet locating probe application for tissue biopsy or resection, a zig-zag configuration can allow the probe to have a narrow tip that can be inserted into an incision, while still permitting improved accuracy by measuring fields at a location slightly off the probe axis, which would correspond to sensor array axis 224. The latter can be useful in situations where the gradients in the ambient field are unimportant.

In FIG. 2B, four multi-axis magnetic field sensors 216A-D are arranged in a linear fashion, i.e., so that a central axis 228A-D of each of the four sensors coincide with the common sensor array axis 230. Advantages of a linear arrangement in general are discussed above in the Formulation of Inverse Algorithm section. However, it is again noted that if sensors 216A-D are placed too far apart, the farthest sensors, e.g., sensors 216C-D, may be so far from the magnet that the magnetic field produced by the magnet may be overwhelmed by the ambient magnetic field of the Earth. In this case, the readings of the distant sensors 216C-D may not differ by more than the sensor error or the gradient in the ambient field, thereby rendering an accurate solution infeasible. In addition, one method of accounting for Earth's ambient magnetic field assumes that the ambient field can be modeled by a simple function (e.g., linear or quadratic) over the entire length of the arrangement. The validity of this assumption becomes questionable as either the lengths (for linear arrays) or, for planar arrays (e.g., as shown in FIG. 2C), the area of the region containing the sensors increases.

In FIG. 2C, magnetic field sensors 220A-D are arranged in non-linear, planar arrangement 212. It is noted that although the sensors 220A-D are shown with a uniform spacing, uniform spacing is not required. Those skilled in the art will appreciate that although four magnetic sensors 208A-D, 216A-D, 220A-D are shown for each of sensor arrangements 200, 204, 212 of FIGS. 2A-C, a different number of sensors may be used in each, depending upon the redundancy desired and the number of field channels each sensor has.

Moving Sensor Variation of Linear Sensor Configuration

Within reasonable limits, the accuracy of the algorithms described above can be improved by calibrating more accurately and consistently or by increasing the number of sensors beyond the minimum number (e.g., three or four) necessary to obtain a solution. Another technique for accomplishing the same goals is to provide a single magnetic filed sensor that moves in a reciprocating or other oscillatory manner. Multiple readings may then be obtained from the moving sensor at various locations along its travels. For example, FIG. 3 shows an example of a magnet sensing apparatus 300 that utilizes this technique. In apparatus 300, a magnetic field sensor 304 may be movably engaged with a linear track 308 so as to be movable along a sensor axis 312. Field strength values are obtained as sensor 304 moves rapidly up and down track 308 in a reciprocating fashion. A single moving sensor configuration, such as shown in FIG. 3, can yield at least three advantages. First, a large number of data points can be obtained from a large number of sensor locations, thereby improving accuracy. Second, by using a single sensor, the self-consistency of the field measurements is essentially guaranteed, reducing the accuracy required of the calibration procedure. Third, only one set of electronics (amplifiers, other support circuits, and analog-to-digital converters) is needed.

That said, these advantages can come at the cost of providing a mechanism 316 for rapidly moving magnetic field sensor 304 and measuring its instantaneous position. Mechanism 316 should avoid introducing stray magnetic fields that compromise the measurements of the field created by the magnet to be located. An exemplary embodiment of mechanism 316 may include an air-driven linear motor made of non-magnetic materials. Another exemplary embodiment of mechanism 316 may utilize a so-called ultrasonic motor. An electric motor may also be used in mechanism 316, particularly if the motor is not located too closely to sensor 304 and/or if the high frequency magnetic field it generates is removed by filtering.

Display of Magnet Position and Orientation

FIG. 4A illustrates an embodiment of a locating system 400 of the present invention that includes a self-contained handheld locating probe 404 and a plurality of items that emit energy that can be sensed by the locating probe. In this case, the items are magnets 408A-D, such that locating probe 404 is a magnet locating probe configured to sense the magnetic field emitted by each of magnets 408A-D. In the scenario shown, magnets 408A-D function as fiducial markers bracketing a tumor 412 destined for excision from a breast 416 of a patient 420. Probe 404 illustrates a number of features that can be implemented to aid a user of the probe, e.g., a surgeon or physician's assistant, in locating each of magnets 408A-D during a procedure for excising tumor 412. Referring to FIG. 4B, and also to FIG. 4A, probe 404 includes a housing 422 that contains a linear arrangement of magnetic field sensors 424A-D in the manner of the linear arrangement shown in FIG. 1. This linear arrangement is selected to facilitate both compensation for gradients in the ambient field and easy manipulation of probe 404 by its user.

A variety of techniques can be used to display the calculated position r of any one of magnets 408A-D relative to, e.g., the tip 404A of probe 404 or another desired reference point. For example, probe 404 may include one or more displays 426, 428, 430 that display or otherwise indicate information to the user regarding the location of any one of magnets 408A-D relative to tip 404A of probe 404. In the embodiment shown, display 426 is an LCD numerical display that shows the distance from tip 404A to, in the case shown, magnet 408A. Similarly, in this embodiment, display 428 includes a series of display elements 432A-C, e.g., LEDs, that indicate whether tip 404A of probe 404 is over the target, substantially at the target, or under the target. It is noted that the target may be the location of magnet 408A itself or a location at some predetermined offset from the magnet, e.g., a pre-established resection margin 436 located outward from magnets 408A-D. Display 430 includes a series of display elements 438A-E, e.g., LEDs, spaced around the circumference of probe 404 that indicates the azimuth angle (pointing angle relative to the longitudinal probe axis 440) by lighting an appropriate one of the display elements. Similar schemes can be used to display magnet orientation.

It is anticipated that many surgeons using a locating device of the present invention will not want to have to constantly change their gaze from the patient to a display. Consequently, a surgical type magnet locating apparatus, such as probe 404 of FIG. 4A may include a purely aural display that encodes information, such as distance and azimuth angle (orientation), with different sounds. For example, and referring to FIGS. 4A and 4B, probe 404 may include one or more sound generators 444 that generates particular sound effects based on positional and azimuthal information generated by a processor 448, e.g., using the algorithms described above and below. The at least one sound generator 444 may communicate with a corresponding speaker 452 (not shown) that produces the actual sounds.

In an exemplary embodiment, probe 404 may communicate azimuthal information using variously pitched sounds generated by sound generator 444. For example, the pitch may be very deep (representing a "null") when probe 404 is pointing directly at one of magnets 408A-D. Then, the pitch may increase as the pointing direction of probe 404 moves away from a particular magnet 408A-D. If desired, distance can be simultaneously indicated, e.g., with a "Geiger-counter-like" sound volume modulation scheme in which the sound generator 444 switches the pointing angle tone on and off at a faster rate as probe 404 gets closer to a corresponding magnet 408A-D. These qualitative indications should be sufficient for applications in which a user is trying to quickly determine the position of one of magnets 408A-D. The magnet position can be quickly determined by moving probe tip 404A until it is pointing directly at the desired magnet 408A-D, as would be indicated by a deeply pitched sound as just discussed.

In conjunction with distance and/or other proximity-to-magnet and probe/magnet orientation displays, a magnet locating apparatus of the present invention, e.g., probe 404 of FIGS. 4A and 4B, may optionally include a feature that allows a user to input a distance offset for processor 448 to use in determining the distance to display on display 426 and in determining which display element 432A-C of display 428 to activate. For example, probe 404 may include an offset input interface 452 that includes, e.g., a set of push buttons (shown), wheel, dial, keypad, etc., in communication with processor 448. As the user inputs the offset into probe 404 using input interface 452, the value of the offset may be displayed on display 426. In the context of the push button type input interface 452 shown, each push of either the "+" or "−" button may cause the offset and display 426 to, respectively, increment or decrement by a predetermined amount, such as 0.1 mm, for example.

To illustrate the use of the distance offset, say a resection margin 436 of FIG. 4A is to be located 1.1 mm radially outward of each magnet 408A-D and the user wants to know when tip 404A of probe 404 is exactly at the margin. In this case, the user could either use no distance offset and simply watch display 426 to see when it indicates the distance to the magnet is 1.1 mm or input a distance offset of 1.1 mm (or −1.1 mm depending on the sign convention used) and use any one or more of display 426, visual location display 428 and the aural distance display (in the example above, the Geiger-counter-like technique).

In the latter scenario in which the desired distance is programmed into the probe, the user could rely on visual displays 426, 428 and the aural distance display to determine when the desired resection margin has been achieved.

Figure 5:
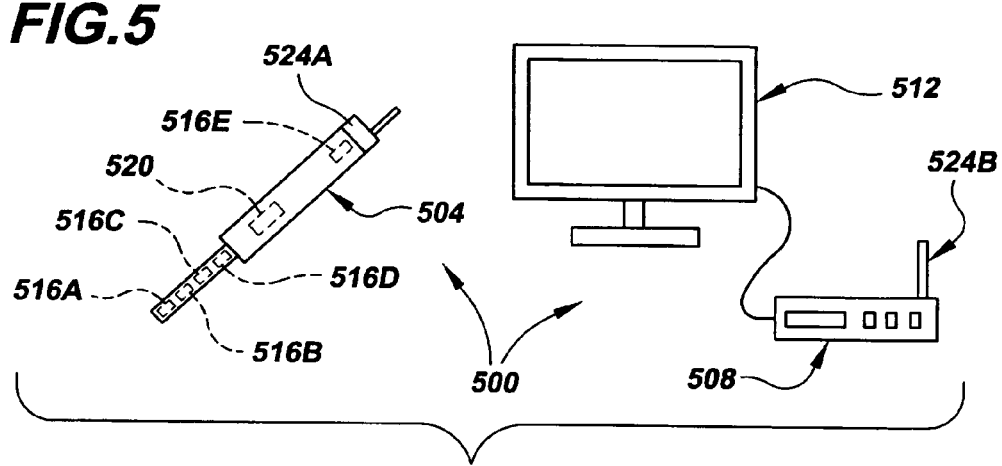
FIG. 5 is a schematic diagram of an alternative magnet locating apparatus of the present invention that includes a dumb handheld probe and a smart remote base station.

FIG. 5 illustrates an alternative locating apparatus 500 of the present invention that includes a "dumb" handheld probe 504 in communication with a "smart" base station 508. Base station 508 may be in communication with a suitable display device 512, such as the flat panel monitor shown, that visually displays various information regarding the use of handheld probe 504, such as the position and/or orientation of the probe relative to each of one or more magnets (not shown). Base station 508 and/or display 512 may also be capable of aurally communicating various information regarding the use of probe 504, such as the aural distance and azimuth information discussed above in connection with magnet locating system 400 of FIGS. 4A and 4B. As those skilled in the art will readily appreciate, base station 508 and display 512 may be physically separate units as shown or, alternatively, may be incorporated into a single integrated unit. Indeed, such an integrated unit (not shown) may be a general purpose personal computer or the like.

Handheld probe 504 may contain a plurality of magnetic field sensors 516A-E that may be similar to sensors 112A-D, 424A-D discussed above. Base station 508 may include a processor 520 that receives information collected by sensors 516A-E and implements various algorithms for calculating position and orientation of probe 504 and calibrating the probe. Such algorithms may be the algorithms discussed above, or may be entirely different suitable algorithms. Probe 504 may communicate information collected by sensors 516A-E to base station 508 either in a wired (tethered) manner or wirelessly, e.g., using radio frequency, infrared or other communication technology suitable for the environment in which system 500 is used. In the embodiment shown, each of probe 504 and base station 508 includes a corresponding respective radio-frequency transceiver 524A-B enabling wireless communication. Those skilled in the art will readily understand how to implement various wireless technologies in system 500.

Figure 6A:
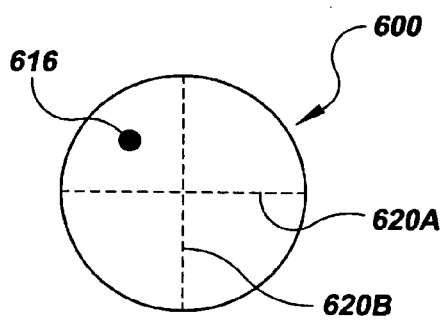
FIG. 6A is a diagram illustrating a real-time pointing direction image that the display device of FIG. 5 may present to a user.
Figure 6B:
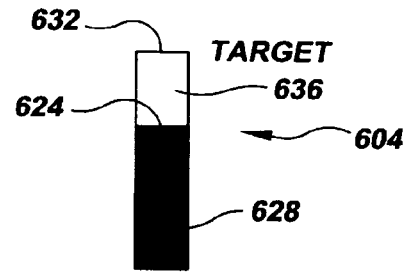
FIG. 6B is a diagram illustrating a real-time distance image that the display device of FIG. 5 may present to a user.

Referring to FIGS. 6A-D, and also to FIG. 5, FIGS. 6A-6D illustrate various real-time graphical images 600, 604, 608, 612 that processor 520 may cause to be displayed on display device 512, e.g., simultaneously, at differing times, or in various combinations. Graphical image 600 of FIG. 6A shows the current pointing direction of handheld probe 504. Relative to graphical image 600, to point probe 504 directly at a particular magnet, a user manipulates the probe so as to center a dot 616, which in this case represents the tip of the probe, in a pair of cross-hairs 620A-B. Graphical image 604 of FIG. 6B shows the current distance-to-magnet, with the upper edge 624 of the dark portion 628 representing the tip of probe 504 (or any other reference point) and the upper boundary 632 of the rectangular region 636 representing the location of the magnet. As the user moves the tip of probe 504 closer to the magnet, upper edge 624 of dark portion 628 moves closer to upper boundary 632. When the tip of probe 504 is essentially at the magnet, the entire rectangular region 636 is dark.

Figure 6C:
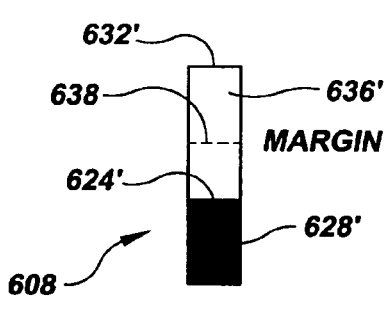
FIG. 6C is a diagram illustrating an alternative real-time distance image that the display device of FIG. 5 may present to a user.

Real-time graphic image 608 of FIG. 6C is similar to graphic image 604 of FIG. 6B, except that it includes an indicator 638 that represents the location of a preset margin, e.g., resection margin 436 of FIG. 4A. The location of the preset margin relative to the magnet may be input into system 500 of FIG. 5 in a manner similar to the inputting of a distance offset into self-contained probe 404 using an offset input interface (not shown) that may be similar to offset input interface 452 of FIGS. 4A and 4B. Like graphic image 604 of FIG. 6B, upper edge 624' of dark portion 628' of FIG. 6C moves upward toward upper boundary 632' of rectangular region 636' in real time as the tip of probe 504 (or other reference point) moves toward the preset margin and the magnet.

Figure 6D:
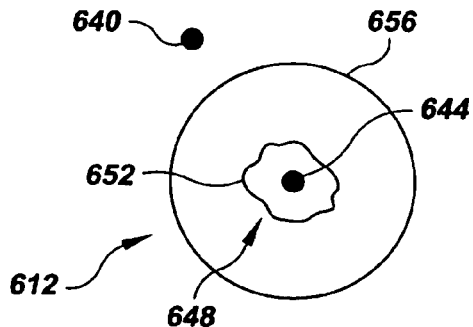
FIG. 6D is a diagram illustrating a real-time pictorial image of pertinent information that the display device of FIG. 5 may present to a user.

Graphical image 612 of FIG. 6D shows in real time the current relationship between the probe-tip location 640, a fiducial marker magnet (depicted at 644) embedded in a tumor (depicted at 648), tumor margin (depicted at 652) (if known), and a predetermined surgical resection margin (depicted at 656). Information regarding the size and shape of the tumor, i.e., tumor margin location 652, and the magnet location 644 relative to the tumor margins may be obtained from various imaging equipment, such as CAT-scan equipment, x-ray equipment, ultrasound equipment, magnetic resonance imaging equipment, etc. and preloaded into system 500 prior to performing a particular medical procedure. The location of resection margin 656 may be input into system 500 as discussed above in connection with FIG. 6C, or may be input into the system using other means, such as graphical input device (not shown) that, e.g., allows a technician, surgeon, etc. to input the margin by essentially superimposing the margin onto one or more images acquired by an imaging device. Those skilled in the art will readily appreciate that there are a number of ways to input resection margin location 656 into system 500. In FIG. 6D, as a user moves the tip of probe 504, current probe-tip location 644 moves relative to tumor margin location 652, magnet location 644, and resection margin location 656 depicted in image 612.

In addition to the fiducial marker application discussed above, a magnet locating apparatus of the present invention may be used in a number of other applications. For example, in the medical field, such additional applications include tracking the movement of an internal organ, e.g., during the performance of a surgical procedure on or in close proximity to that organ, and tracking the movement of various items within various body cavities. These applications are described below.

For example, instead of a fiducial marker magnet, e.g., any one of magnets 408A-D of FIG. 4A above, being used to define an excision margin, |a magnet| may be used for other locating purposes. For example, a magnetic marker could be inserted next to or inside a tumor to be treated using targeted drug delivery or radiation therapy. Prior to treatment, a locational apparatus, which may include any one or more aspects of the magnetic field sensing scheme described above in connection with the tissue excision example, could be used to determine the position of the tumor relative to a catheter used for drug delivery or a targeted radiation therapy system. The fact that the marker moves along with the surrounding tissue permits real-time tracking and targeting of moving tissues. One important example of this is tracking of organ motion due to respiration, cardiac activity, or changes in body position of the patient.

Figure 7:
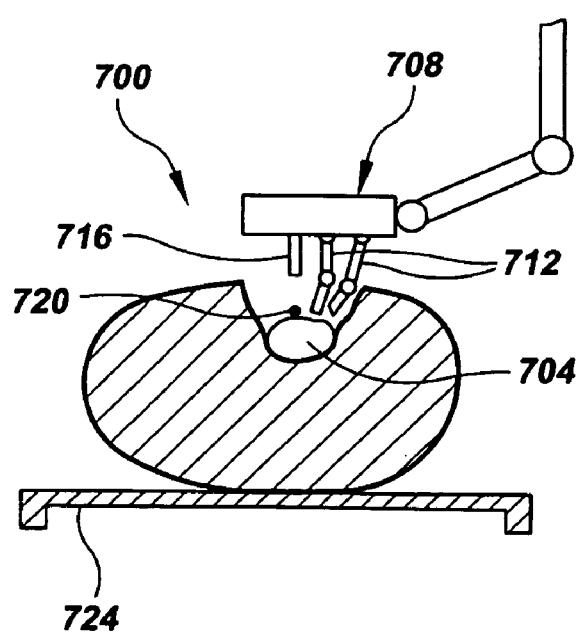
FIG. 7 is a partial cross-sectional view/partial high-level schematic diagram of a human body and a magnet locating system of the present invention used to track motion of an internal organ during surgery.

In this connection, FIG. 7 illustrates use of a locational system 700 of the present invention to track the movement of an internal organ, in this case a heart 704, during the performance of heart surgery using a robotic surgical device 708 having a plurality of tools 712. In this application, system 700 includes a magnet locating apparatus 716 and magnetic marker 720 secured to heart 704 in a manner that it accurately follows the movement of the heart, e.g., by stitching. Emissive reference marker 720 may be a body that emits energy capable of being sensed and used to determine the position and/or orientation of the body relative to magnet locating apparatus 716 and/or the position of the apparatus relative to the body. Those skilled in the art will appreciate that magnet locating apparatus 716 may be a magnetic locating device comprising one or more magnetic field sensors (not shown) and a processor for performing the necessary location, orientation and calibration algorithms, such as the algorithms discussed above.

In this example, locational system 700 assists a surgeon (not shown) in robotic heart surgery in which it is highly desirable to attenuate the impact of cardiac motion by moving the surgical tools 712 so as to maintain a constant position relative to the surface of heart 704. Magnet locating apparatus 716 may be attached to robotic surgical device 708 or, alternatively, may be fixedly secured to another support, such as an operating table 724, a movable support, or the like. Another application (not shown) involves attaching a magnetic marker similar to marker 720 to the surface of a patient's liver during abdominal surgery to provide a real-time indication of liver movement due to respiration or surgical manipulation. The resulting information could be used for co-registration of preoperative anatomic images during image-guided surgery. Those skilled in the art will readily appreciate that the heart and liver are just two examples of internal organs that may be tracked using a magnet locating system of the present invention. Other examples include the diaphragm, lungs, and stomach, to name a few.

Figure 8:
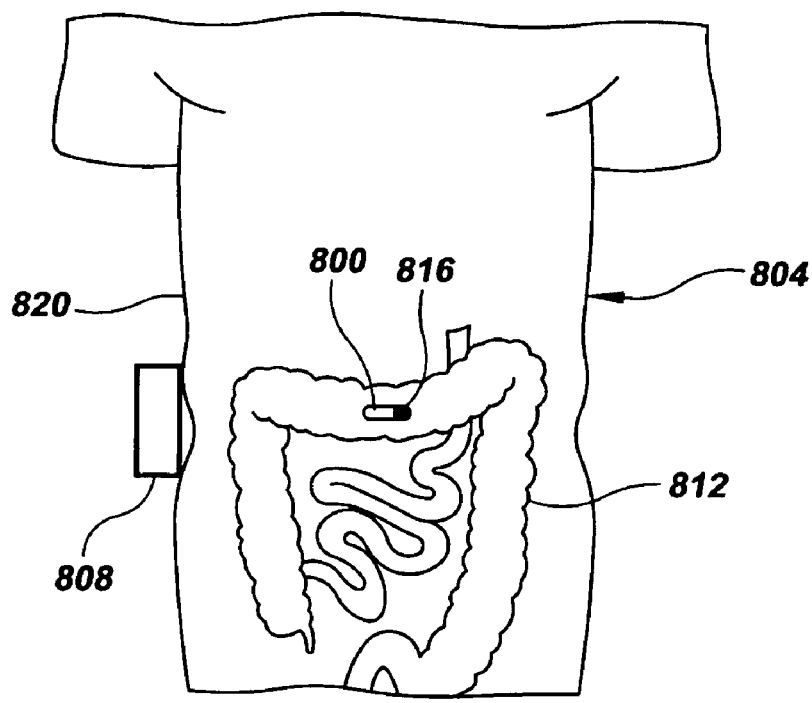
FIG. 8 is a partial schematic diagram of a human body and a magnet locating system of the present invention for tracking the movement of an untethered device within the body.

While the uses of a magnet locating system of the present invention described above have involved placing one or more fiducial magnetic markers within tissue or attaching such magnets to internal organs, FIG. 8 illustrates the tracking of an untethered medical device 800 within a human body 804 using a magnet locating apparatus 808 of the present invention. (Generally, the term "untethered" is used herein to distinguish these devices from catheters, probes and other devices that are inserted into patients' bodies but which include portions that extend outside the body so that the devices can be manipulated, retrieved, or supplied with electrical power.) In FIG. 8, device 800 is shown in the large intestine 812 of body 804 and includes a magnetic reference marker 816 detectable and locatable with magnet locating apparatus 808. Device 800 may have gotten into large intestine 812 by the patient having swallowed it or by other means as appropriate. Apparatus 808 may be positioned either outside or inside of the patient's body 804 as the particular procedure requires and may utilize any one or more of the aspects of the sensing scheme and locating and calibrating algorithms described above in connection with the tissue excision example. In a particular application, untethered medical device 800 comprises a suitably shaped body that, in conjunction with magnet locating apparatus, provides a non-invasive measurement of gastrointestinal motility. A sensor configuration that may be utilized for this application is a two-dimensional array similar to one shown in FIG. 2C that may be mounted, e.g., on the side 820 (shown), back, or abdomen of the patient's body 804.

In another application, untethered device 800 may include a drug repository, e.g., capsule or implantable micro electro-mechanical system (MEMS) pump, for example, that moves to different parts of body 804. In this application, magnet locating apparatus 808 can be used to determine when the drug repository is in an appropriate place to deliver treatment. At that point, device 800 could be remotely commanded to deliver the drug, e.g., by actuating a suitable release mechanism, such as actuating the MEMS pump.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. An apparatus for locating a margin located within a living body an offset distance from a magnetic marker located in the living body and having a magnetic field, the apparatus comprising:
    a probe that includes:
        (a) a structure having a reference point positionable at the margin;
        (b) at least one magnetic field sensor configured to generate an output signal as a function of the magnetic field of the magnetic marker;
        (c) a selector for presetting the offset distance between the margin and the magnetic marker;
        (d) a central processor configured to calculate a location of the margin relative to said reference point as a function of said output signal and the offset distance; and
        (e) a display operatively coupled to said central processor and configured to display information about said location.

2. An apparatus according to claim 1, wherein said display is a visual display.

3. An apparatus according to claim 2, wherein said visual display comprises a portion that indicates when said reference is at the margin.

4. An apparatus according to claim 1, wherein said display is an aural display.

5. An apparatus according to claim 4, wherein said aural display comprises a sound having a volume modulation frequency that varies as a function of said location.

6. A method of determining the location of a magnet using a plurality of magnetic field sensors, comprising:
    (a) determining whether any one or more of the plurality of magnetic field sensors has saturated;
    (b) calculating the location of the magnet using only ones of the plurality of magnetic field sensors that are not saturated;
    (c) determining whether a sufficient number of the plurality of magnetic field sensors remain unsaturated so as to permit a solution; and
    (d) if an insufficient number of the plurality of magnetic field sensors remain to permit a solution, calculate the location of the magnet using the ones of the plurality of magnetic field sensors that are not saturated and assuming a magnetic gradient does not exist.

* * * * *